United States Patent

Rao et al.

[11] Patent Number: 5,520,611
[45] Date of Patent: May 28, 1996

[54] ILLUMINATED RETRACTOR

[76] Inventors: Shekar Rao, 17 Pheasant Ct., Appleton, Wis. 54915; Dilip K. Tannan, 1615 Deerfield Dr., Oshkosh, Wis. 54904

[21] Appl. No.: 167,161

[22] Filed: Dec. 16, 1993

[51] Int. Cl.⁶ ............................................. A61B 17/02
[52] U.S. Cl. ..................... 600/245; 600/246; 600/212; 600/235
[58] Field of Search ................... 128/20, 23, 11, 128/13, 16, 18; 600/212, 245, 235, 210, 246; 606/61

[56] References Cited

U.S. PATENT DOCUMENTS

| | | | |
|---|---|---|---|
| 3,796,214 | 3/1974 | Davis | 128/6 |
| 3,809,072 | 5/1974 | Erser et al. | 128/23 |
| 4,086,919 | 5/1978 | Bullard | 128/6 X |
| 4,344,419 | 8/1982 | Burgin | 128/18 |
| 4,562,832 | 1/1986 | Wilder et al. | 128/20 |
| 4,597,030 | 6/1986 | Brody et al. | 128/20 X |
| 4,996,976 | 3/1991 | Nakagawa | 128/16 |
| 5,035,232 | 7/1991 | Lutze et al. | 600/245 |

FOREIGN PATENT DOCUMENTS

| | | | |
|---|---|---|---|
| 2570266 | 3/1986 | France | 128/20 |
| 3736066 | 11/1988 | Germany | 128/20 |

OTHER PUBLICATIONS

Exhibit A —From a catalog by Walter Lorenz Company showing lighted dental retractor.
Exhibit B —from a catalog by Walter Lorenz Surgical, Inc. showing neurosurgery retractor.

Primary Examiner—Richard J. Apley
Assistant Examiner—John P. Leubecker
Attorney, Agent, or Firm—Donald Cayen

[57] ABSTRACT

An illuminated retractor provides illumination to a surgical field deep in a cavity in a patient's back. The illuminated retractor has a first blade that is inserted into the cavity and hooks on a vertebrae. A second blade lies on the patient's back. Weights applied to the second blade hold the cavity open. Fiber optic cables are embedded in the illuminated retractor. Output ends of the fiber optic cables terminate at a step in the first blade. Input ends of the fiber optic cables extend from a second blade and are gathered into a fitting. By connecting the fitting to a source of illumination, light is provided by the fiber optic cables output ends to the surgical field. The illuminated retractor first blade is smooth and occupies minimum space so as to not interfere with the surgeon's fingers or instruments.

11 Claims, 3 Drawing Sheets

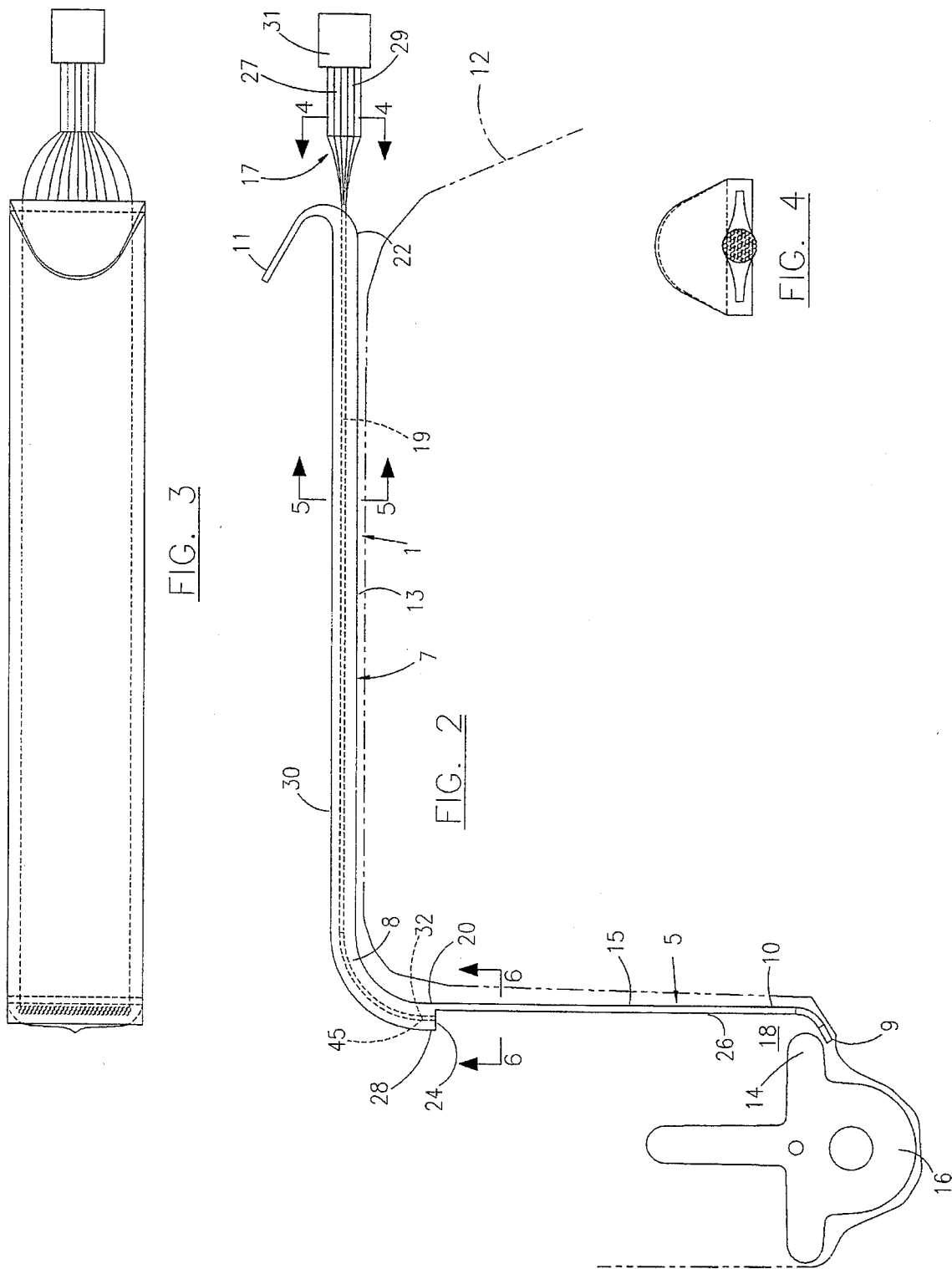

ILLUMINATED RETRACTOR

BACKGROUND OF THE INVENTION

1. Field of the Invention

This invention pertains to medical instruments, and more particularly to apparatus for illuminating body areas undergoing surgery.

2. Description of the Prior Art

It is imperative that adequate lighting be provided to affected regions during surgical procedures. However, overhead room lighting is rarely sufficient for operating purposes. Accordingly, various types of supplemental lighting equipment have been developed that suits different medical illumination requirements.

For example, Walter Lorenz Surgical, Inc. of Jacksonville, Fla., manufactures surgical retractors useful in oral surgery that include a fiber optic cable. The fiber optic cable is clipped to an external surface of the retractor. One end of the fiber optic cable is connected to a source of illumination. The output end of the fiber optic cable is positioned to direct a beam of light on the mouth area being treated. Although useful, the externally clipped fiber optic cable is prone to being bumped and misdirected during use.

A headlight lighting system is manufactured by the Luxtec Corporation of Worcester, Mass. In that type of system, the output end of a fiber optic cable is connected to a headband worn by a surgeon. The fiber optic cable supplies light to a headlight on the headband. The headlight may be fixed or moveable to suit different requirements. By moving his head and/or the headlight, the surgeon is able to direct light to the region where he is working.

During back surgery, the muscles and tissue adjacent the spine are cut to provide access to the affected vertebrae. It is a common practice to employ a unilateral retractor to hold the muscles and tissue in a position that creates a working cavity. To minimize post-operative discomfort and complications, the incision in the back muscles and tissue is kept to a minimum, often one inch long or less. A disadvantage of such a small incision is that the area of the working cavity is small relative to the cavity depth. Consequently, it is often difficult to provide sufficient illumination to the vertebrae at the bottom of the cavity. That is true even with direct light from a surgeon's headlight. The problem is aggravated by the presence of the surgeon's fingers, his instruments, and the retractor within the cavity, because those items tend to block the incoming light and cast shadows over the surgical field.

Clipping a fiber optic cable onto the retractor in the manner of orthodontic instruments is not an acceptable solution, because of the potential for the fiber optic cable to be bumped. In addition, the prior fiber optic cable design would decrease the volume within the cavity that is available to the surgeon's fingers and instruments. Another drawback of the prior fiber optic cable and clip combination is that the loss of light from a small spatter of blood or other fluid on the output end of the fiber optic cable would be intolerable.

Thus, a need exists for an improved surgical lighting system.

SUMMARY OF THE INVENTION

In accordance with the present invention, an illuminated retractor is provided that greatly increases the illumination within a body cavity. This is accomplished by apparatus that integrates light conductors into a unilateral retractor.

In one aspect of the invention, the illuminated retractor has the general mechanical form of a retractor commonly used in lumbar laminotomy surgery. However, the illuminated retractor of the present invention has a first blade that is made up of two sections: a relatively thin first section and a slightly thicker second section. The two sections are joined to each other such that respective inside surfaces thereof are coplanar. Accordingly, there is a step between the outside surfaces of the first and second sections. The step can be located at any desired location on the first blade. The step may be perpendicular or oblique to the outside surfaces of the two sections. The free end of the first section has a bent point. The illuminated retractor further has a second blade of the same thickness as the second section of the first blade. The second blade joins the first blade second section and may be generally perpendicular thereto. There is a hook on the lateral end of the second blade.

The light conductors are a number of fiber optic cables preferably arranged side by side and encapsulated into the retractor material. The fiber optic cables are located near the outside surface of the second blade and extend for its full length. The fiber optic cables also lie near the outside surface of the second section of the first blade. The fiber optic cables terminate at the step in the first blade.

The fiber optic cables emerge from the lateral end of the second blade, and they are bundled together outside of the second blade into a generally circular cable. The cable terminates in a fitting that can be connected to a source of illumination.

In use, the illuminated retractor first blade is inserted into a cavity in a patient's back, when it occupies minimum volume. The inside surface of first blade is placed against the cavity wall, and the point is fit under the facet of the vertebrae undergoing the operation. The retractor second blade is laid on the exterior of the patient's back, with the second blade inside surface resting on the patient. Weights hung on the second blade hook cooperate with the first blade point and vertebrae facet to maintain the cavity in an open condition. The fiber optic cable fitting is connected to a source of illumination. The output ends of the fiber optic cables throw light directly onto the vertebrae and surrounding area at the bottom of the cavity. Because the fiber optic cable output ends are only a short distance from the surgical field, the light from them is not readily blocked by the surgeon's fingers or instruments. Consequently, the surgeon has ample light at all times in the area where he is working. Moreover, the fact that the fiber optic cables form an integral part of the retractor results in a smooth retractor surface inside the cavity that does not interfere with the operating procedures.

The method and apparatus of the invention, using light conductors integrated into a surgical instrument, thus enhances the illumination of a body cavity during surgery. The probability of light from the illuminated retractor being blocked and casting a shadow on a surgical field is relatively remote, even though the surgeon's fingers and instruments are constantly moving within the cavity.

Other advantages, benefits, and features of the present invention will become apparent to those skilled in the art upon reading the detailed description of the invention.

BRIEF DESCRIPTION OF THE DRAWINGS

FIG. 2 is a side view of the illuminated retractor.

FIG. 3 is a top view of FIG. 2.

FIG. 4 is a cross sectional view taken along line 4—4 of FIG. 2.

DETAILED DESCRIPTION OF THE PREFERRED EMBODIMENT

Figure 1:
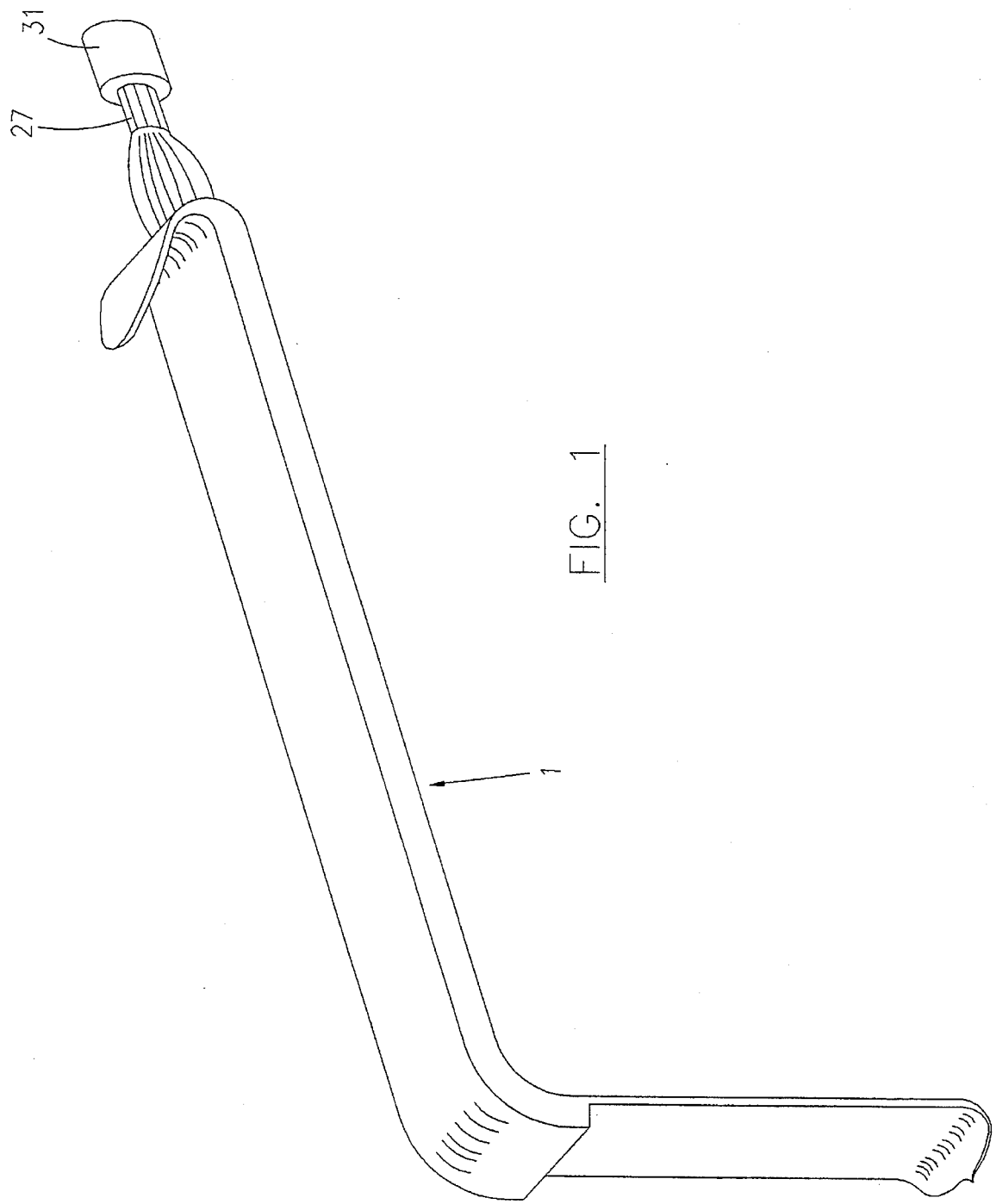
FIG. 1 is a perspective view of the illuminated retractor of the present invention.
Figure 5:
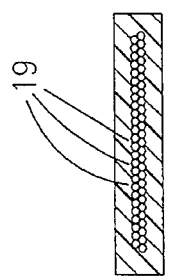
FIG. 5 is an enlarged cross sectional view taken along line 5—5 of FIG. 2.
Figure 6:
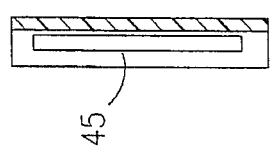
FIG. 6 is an enlarged cross sectional view taken along line 6—6 of FIG. 2.

Although the disclosure hereof is detailed and exact to enable those skilled in the art to practice the invention, the physical embodiments herein disclosed merely exemplify the invention, which may be embodied in other specific structure. The scope of the invention is defined in the claims appended hereto.

Referring to FIGS. 1–6, an illuminated retractor 1 is illustrated that includes the present invention. The particular illuminated retractor 1 shown is based on a Taylor spine unilateral retractor used in lumbar laminotomy surgery.

The illuminated retractor 1 has first and second flat blades 5 and 7, respectively, that meet at a curved junction 8. The blades 5 and 7 are shown as being at right angles to each other. However, the blades may make an oblique angle of up to approximately 135 degrees if desired. The first blade 5 is composed of two sections, a relatively thin first section 10 and a thicker section 20. The first section 10 terminates in a bent point 9. The lateral end 22 of the second blade 7 terminates in a hook 11. The first and second sections 10 and 20, respectively, of the first blade 5 have a common coplanar inside surface 15. The second blade 7 has an inside surface 13 that blends smoothly into the surface 15 around the junction 8. The first blade first section has an outside surface 26. The first blade second section 20 has an outside surface 28 that is generally parallel to the surface 26. The outside surface 28 blends smoothly around the junction 8 into the outside surface 30 of the second blade 7. There is a step 24 between the outside surfaces 26 and 28 of the first blade.

The illuminated retractor 1 further comprises an illumination system 17 that is integrated into the blades 5 and 7. In the preferred embodiment, the illumination system 17 is comprised of a number of small diameter fiber optic cables 19. The fiber optic cables 19 are arranged in one or more parallel flat rows. Output ends 32 of the fiber optic cables terminate at a small flat profile lens 45 that is embedded in the second section 20 at the step 24. The input ends 27 of the fiber optic cables extend from the lateral end 22 of the second blade 7 proximate the hook 11. The fiber optic cable input ends 27 are gathered together into a generally circular bundle 29. A known fiber optic fitting 31 is assembled to the bundle 29.

The illuminated retractor 1 may be manufactured from any material that is sterilizable in an autoclave. Satisfactory materials include surgical grade synthetic plastics such as ebonite. Metal is not a desirable material, because metals have undesirably high coefficients of thermal conductivity that tend to transmit heat from the fiber optic cables to the patient's body. The fiber optic cables 19 are molded integrally into the retractor blades 5 and 7. The fiber optic cables are therefore protected from harm during use, cleaning, and other handling. Further, they do not interfere with the surgeon's fingers or instruments.

The illuminated retractor 1 is used in substantially the same manner as the prior Taylor unilateral retractors. An incision is made in the erector spinae and unlying muscles of the patient's back 12. The illuminated retractor first blade 5 is inserted into the incision, and the point 9 is placed under the facet 14 of the adjacent vertebrae 16 to be operated upon. The second blade 7 rests on the patient's back 12. The hook 11 overhangs the side of the patient's back. By hanging weights, not shown, on the hook, the retractor acts as a lever that pulls the muscles and other tissues adjacent the surface 15 of the first blade away from the midline spinous process of the vertebrae. Consequently, the area 18 of the incision opens for examination and surgery.

The fitting 31 at the input ends 27 of the fiber optic cables 19 is connected to a source of illumination. The light is conducted by the fiber optic cables to their output ends 32 at the flat profile lens 45. Light emitted from the lens illuminates the vertebrae 16 and the surrounding surgical field 18. In that manner, light is always available at the operating region even if overhead lighting is broken by the operating instruments or the surgeon using them.

Figure 7:
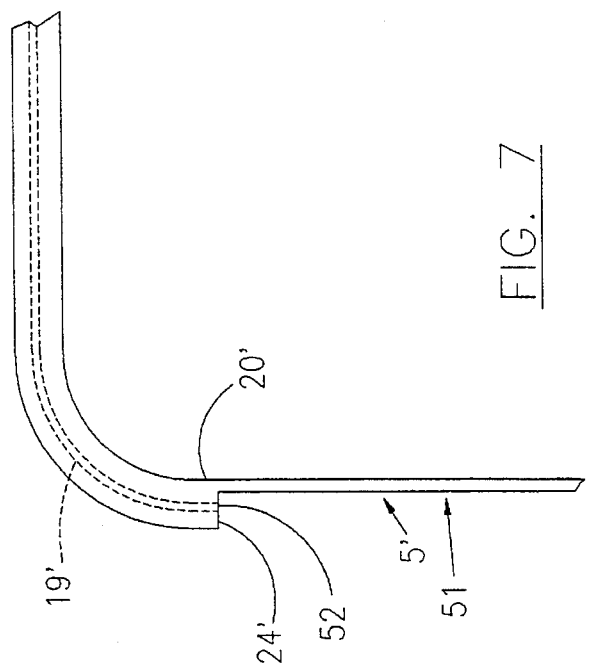
FIG. 7 is a partial side view on an enlarged scale of the illuminated retractor showing an alternative design for the output ends of the fiber optic cables.

In some situations, it may be desirable that the output ends of the fiber optic cables terminate exactly at the step between the outside surfaces of the first and second sections of the first blade. In those cases, as shown in FIG. 7, the flat profile lens 45 of the illuminated retractor 1 of FIGS. 1–6 is removed. The modified illuminated retractor 51 of FIG. 7 has fiber optic cables 19' that are embedded into the second section 20' of the first blade 5' up to the step 24'. Thus, the output ends 52 of the fiber optic cables 19' are generally coplanar with the step 24'.

The step between the outside surfaces of the first and second sections of the first blade need not be perpendicular to those surfaces. Looking at FIG. 8, an illuminated retractor 53 has a step 54 that is oblique to the outside surfaces 55 and 57 of the first and second sections 59 and 61, respectively, of the first blade 63. The fiber optic cables 67 are embedded in the second section 61 near its outside surface 57 and terminate at the oblique step 54. The output ends 69 of the fiber optic cables 67 are thus also oblique to the outside surfaces 55 and 57.

Figure 8:
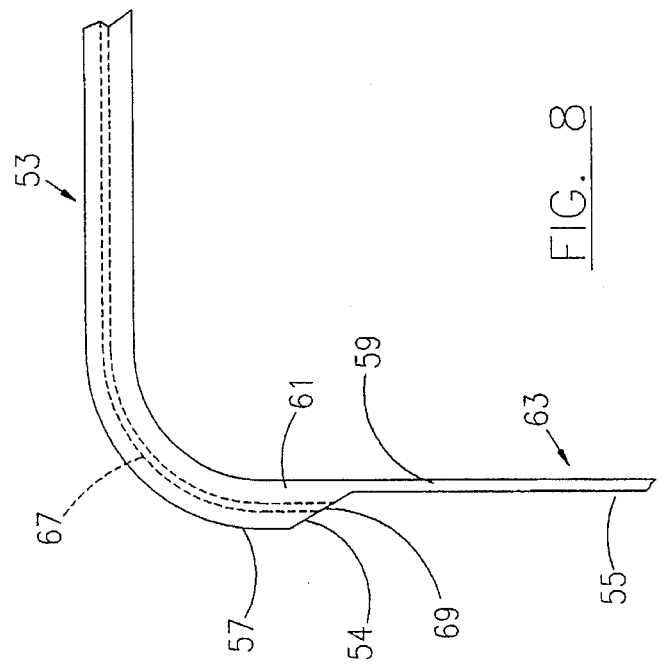
FIG. 8 is a view similar to FIG. 7, but showing another construction for the output ends of the fiber optic cables.

The illuminated retractors 51 of FIG. 7 and 53 of FIG. 8 function in generally the same manner as the illuminated retractor 1 of FIGS. 1–6. However, the illumination requirements of the vertebrae 16 and the rest of the surgical field 18 (FIG. 2) may in certain instances render the illuminated retractors 51 or 53 superior to the illuminated retractor 1 for particular applications.

In summary, the result and advantages of surgical retractors can now be more fully realized. The illuminated retractor of the present invention renders the surgical field well lit during back operations while remaining unobstructive to the surgeon. This desirable result comes from using the combined functions of fiber optic cables and the smooth profile of the illuminated retractor blades. The illuminated retractor can be made in different sizes to suit different patients. Further, the location of the fiber optic cables output ends on the first blade can be varied to suit different applications.

It will also be recognized that in addition to the superior performance of the illuminated retractor, its construction is such as to increase only modestly its cost relative to traditional retractors. Accordingly, hospitals and other medical centers can add the illuminated retractor to their inventories of surgical instruments for only slight additional costs.

Thus, it is apparent that there has been provided, in accordance with the invention, an illuminated retractor that fully satisfies the aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. An illuminated retractor comprising:
   a. a first blade made as a single piece of rigid material comprising:
      i. a first section having first and second parallel side edges, a first thickness bounded by first and second flat parallel planes and a first end that terminates in a bent point and a second end, the first section defining an inside surface coincident with the first plane; and
      ii. a second section having first and second parallel side edges coplanar with the first and second side edges, respectively, of the first section, a second thickness greater than the first thickness and bounded by the first plane and a third flat plane parallel to the first plane, a first end that joins the second end of the first section, and an imperforate inside surface that is coplanar with the inside surface of the first section, the second section defining a step at the first end thereof that extends between the first and second side edges of the second section and between the second and third planes;
   b. a second blade made as a single piece of rigid material integral with the first blade and having first and second side edges coplanar with the first and second side edges, respectively, of the second section of the first blade, a thickness generally equal to the second thickness and bounded by fourth and fifth flat parallel planes, a first end joined to the second end of the first blade second section and extending oppositely of the bent point of the first blade, the second blade lying generally at a right angle to the first blade and having an imperforate inside surface coinicident with the fifth plane, the second blade having a lateral end that defines a hook that extends generally in a direction opposite the direction that the first blade extends from the second blade; and
   c. at least one fiber optic cable embedded in the second blade between the fourth and fifth planes and in the second section of the first blade between the second and third planes, the fiber optic cable having an output end that terminates at the step of the first blade second section, the fiber optic cable having an input end that extends from the second blade lateral end for connecting to a source of illumination.

2. The illuminated retractor of claim 1 wherein the step of the first blade second section makes a right angle with the plane of the first blade first section, and wherein the output end of the fiber optic cable lies generally within the plane of the step.

3. The illuminated retractor of claim 1 wherein the step of the first blade second section defines a sixth plane that makes an oblique angle with and intersects the second plane of the first blade first section, and wherein the output end of the fiber optic cable lies generally within the sixth plane.

4. The illuminated retractor of claim 1 wherein there are a plurality of fiber optic cables arranged in at least one flat row embedded in the second section of the first blade between the second and third planes and between the fourth and fifth planes of the second blade, the fiber optic cables having respective input ends that are gathered together into a circular bundle proximate the second blade lateral end.

5. The illuminated retractor of claim 1 further comprising a flat profile lens embedded in the first blade second section adjacent the step therein, the fiber optic cable output end terminating at the flat profile lens.

6. An illuminated retractor useful in surgery on a person's back comprising:
   a. a first blade made from a single piece of rigid material and having a first section with a first predetermined thickness defined by parallel side edges and inside and intermediate flat parallel surfaces, a first end that terminates in a bent point, and a second end, the first blade further having a second section with parallel side edges and a first end joined to the first section second end, a second thickness greater than the first thickness defined by an imperforate second inside surface coplanar with the first section inside surface and an outside flat surface parallel to the second inside surface, a second end, and a step between the intermediate and outside flat surfaces at the first end;
   b. a second blade made as a single piece of rigid material integral with the first blade and having parallel side edges and flat parallel imperforate surfaces and a first end joined to the second end of the first blade second section and extending oppositely of the point of the first blade and a lateral end that defines a hook that extends in a direction generally opposite the direction that the first blade extends from the second blade; and
   c. light means embedded in the first blade between the inside and outside surfaces thereof and in the second blade between the flat surfaces thereof for conducting a source of illumination to the step.

7. The illuminated retractor of claim 6 wherein the light means comprises a plurality of fiber optic cables, the fiber optic cables having respective output ends that terminate at the step and respective input ends that extend from the second blade second end, the fiber optic cable input ends being bundled together into a fitting, wherein:
   a. the step makes an oblique angle with the outside flat surface of the first blade; and
   b. the output ends of the fiber optic cables terminate in respective oblique angles generally coplanar with the step,
   so that the fitting can be connected to a source of illumination and the fiber optic cables can conduct the source of illumination to the step.

8. The illuminated retractor of claim 6 wherein:
   a. the step makes a right angle with the inside surface of the first blade; and
   b. the first ends of the fiber optic cables terminate in respective right angles generally coplanar with the step.

9. The illuminated retractor of claim 6 wherein the light means comprises:
   a. a lens embedded in the first blade second section adjacent the step; and
   b. a plurality of fiber optic cables embedded in the second section of the first blade and in the second blade, the fiber optic cables having respective output ends that terminate at the lens and respective input ends that extend from the second blade second end, the fiber optic cable input ends being bundled together into a fitting, so that the fitting can be connected to a source of illumination and the source of illumination is conducted to the lens by the fiber optic cables.

10. A method of illuminating a surgical field in a cavity in a patient's back comprising the steps of:

a. incising a small opening in the patient's back adjacent his spine;

b. providing an illuminated retractor comprising the steps of:

i. providing a retractor having first and second generally perpendicular blades each bounded by flat parallel imperforate surfaces with a step formed in the first blade, said first; and ii. embedding in the retractor between the flat parallel surfaces thereof at least one fiber optic cable having an output end that terminates at the step and an input end that extends from the retractor second blade, said first blade terminating in a bent point;

c. inserting the illuminated retractor first blade into the opening in the patient's back and hooking the first blade on the patient's spine;

d. applying a force to the illuminated retractor second blade and opening the cavity and exposing a small surgical field;

e. connecting the fiber optic cable input end to a source of illumination; and f. conducting light from the source of illumination to the fiber optic cable output end and illuminating the surgical field.

11. The method of claim 10 wherein the step of providing an illuminated retractor comprises the further steps of:

a. embedding a flat profile lens in the illuminated retractor adjacent the step therein; and b. terminating the output end of the fiber optic cable at the flat profile lens.

\* \* \* \* \*